(12) United States Patent
Anderson et al.

(10) Patent No.: US 7,998,166 B2
(45) Date of Patent: Aug. 16, 2011

(54) DISTAL PROTECTION DEVICE WITH LOCAL DRUG DELIVERY TO MAINTAIN PATENCY

(75) Inventors: Kent D. Anderson, Champlin, MN (US); Richard S. Kusleika, Eden Prairie, MN (US); Jennifer L. Pavlovic, Afton, MN (US); Chad J. Volk, West Fargo, ND (US); Gary A. Thill, Vadnais Heights, MN (US); Jeannine B. Baden, Mound, MN (US)

(73) Assignee: Tyco Healthcare Group LP, Mansfield, MA (US)

( * ) Notice: Subject to any disclaimer, the term of this patent is extended or adjusted under 35 U.S.C. 154(b) by 456 days.

(21) Appl. No.: 12/174,251

(22) Filed: Jul. 16, 2008

(65) Prior Publication Data

US 2008/0281263 A1    Nov. 13, 2008

Related U.S. Application Data

(63) Continuation of application No. 10/290,426, filed on Nov. 7, 2002, now abandoned.

(60) Provisional application No. 60/337,664, filed on Nov. 7, 2001, provisional application No. 60/337,936, filed on Nov. 7, 2001.

(51) Int. Cl.
*A61M 29/00*    (2006.01)
(52) U.S. Cl. .......... 606/200; 604/269; 604/104
(58) Field of Classification Search .......... 604/508, 604/509, 96.01, 104–107, 265, 266, 269; 606/200, 191, 194, 198
See application file for complete search history.

(56) References Cited

U.S. PATENT DOCUMENTS

| | | | |
|---|---|---|---|
| 5,078,994 A | 1/1992 | Nair et al. | |
| 5,135,516 A * | 8/1992 | Sahatjian et al. | 604/265 |
| 5,624,411 A * | 4/1997 | Tuch | 604/265 |
| 5,709,704 A | 1/1998 | Nott et al. | |
| 5,770,222 A | 6/1998 | Unger et al. | |
| 5,776,100 A | 7/1998 | Forman | |
| 5,820,917 A * | 10/1998 | Tuch | 427/2.1 |
| 6,013,093 A | 1/2000 | Nott et al. | |
| 6,022,336 A | 2/2000 | Zadno-Azizi et al. | |
| 6,106,473 A | 8/2000 | Violante et al. | |
| 6,203,561 B1 | 3/2001 | Ramee et al. | |
| 6,221,672 B1 | 4/2001 | Baugh et al. | |
| 6,231,589 B1 | 5/2001 | Wessman et al. | |
| 6,402,736 B1 | 6/2002 | Brown et al. | |
| 6,436,120 B1 | 8/2002 | Meglin | |
| 6,443,898 B1 | 9/2002 | Unger et al. | |
| 6,498,945 B1 | 12/2002 | Alfheim et al. | |
| 6,620,148 B1 * | 9/2003 | Tsugita | 604/509 |
| 6,663,613 B1 * | 12/2003 | Evans et al. | 604/523 |
| 7,037,332 B2 | 5/2006 | Kutryk et al. | |
| 2001/0018072 A1 | 8/2001 | Unger | |

(Continued)

FOREIGN PATENT DOCUMENTS

WO    WO 96/01591 A1    1/1996
(Continued)

*Primary Examiner* — Laura Bouchelle

(57) ABSTRACT

The present invention provides for a drug delivery mechanism for use with a protection device. The protection device has an expandable filter. The drug delivery mechanism automatically delivers a drug to the filter without requiring the intervention of the operator of the protection device. The drug delivered to the filter facilitates continued filter patency during the medical procedure.

38 Claims, 4 Drawing Sheets

U.S. PATENT DOCUMENTS

| | | |
|---|---|---|
| 2002/0039594 A1 | 4/2002 | Unger |
| 2002/0173819 A1 | 11/2002 | Leeflang et al. |
| 2003/0018294 A1 | 1/2003 | Cox |
| 2004/0127978 A1 | 7/2004 | Sparer et al. |
| 2005/0175707 A1 | 8/2005 | Talton et al. |

FOREIGN PATENT DOCUMENTS

| | | |
|---|---|---|
| WO | WO 01/08743 A1 | 2/2001 |
| WO | WO 03/059205 A2 | 7/2003 |

* cited by examiner

DISTAL PROTECTION DEVICE WITH LOCAL DRUG DELIVERY TO MAINTAIN PATENCY

CROSS-REFERENCE TO RELATED APPLICATIONS

This application is a continuation of application Ser. No. 10/290,426, filed Nov. 7, 2002, the contents of which are hereby incorporated herein by reference, and which claims priority, under 35 U.S.C. §119(e)(1), of provisional application Ser. No. 60/337,664 and application Ser. No. 60/337,936, both previously filed Nov. 7, 2001 under 35 U.S.C. §111(b).

BACKGROUND OF THE INVENTION

1. Field of the Invention

The present invention generally relates to medical devices for filtering or removing matter from within a vascular system and the delivery of drugs to maintain continued filter patency. More specifically, the present invention relates to a protection device having a drug delivery system for facilitating patency of the protection device. This device also relates to any other interventional applications where patency must be maintained. This includes such apparatus as stents, grafts, vessel liners, and guide catheters.

2. Description of Related Art

A protection device, generally, is an expandable filter attached to a hostwire. Protection devices are often employed in interventional cardiology/radiology applications to allow the flow of fluid, such as blood, while preventing the passage of particulate matter, such as emboli. Protection devices are often referred to as distal protection devices where the term "distal" refers to the positioning of the protection device distal to a lesion or treatment site relative to flow in the vessel. The filter portion of existing protection devices may include such items as braided meshes, woven fabrics, perforated films, a plurality of crossing wires, electrospun polymers and any other configuration suitable for filtering.

The performance of the protection device requires that the filter maintain patency. Patency is defined as the ability of the filter to allow the passage of fluid. Patency may refer to a filter at a specific point in time and/or the amount of time that a filter is able to maintain non-occlusiveness. When used in a vascular system, the patency of the filter typically decreases over a period of time. As the pore size of the filter decreases, the patency will decrease relative to that for a greater pore size. For example, in some filters when the maximum pore size is 100 um there may be pores ranging in size from 20 um or less. Such a fine pore size may cause a filter to become occluded by debris. Pores below a crucial pore size may also become occluded by formation of an impermeable fibrous sheet that may close off flow through the pore.

The current art utilizes three different mechanisms for facilitating patency. A mechanism facilitates patency where the mechanism allows greater flow-through, when compared to the performance of a similar filter without the mechanism.

The first mechanism used in the current art involves the pre-application of coatings on the filter used to prevent blood clotting. Such coatings include anti-coagulants, anti-thrombogenics, anti-platelets or other such drugs. One typical drug of this nature is heparin. Even with such coatings the patency of the filter is limited because the drug coating is eventually overcome by clotting forces in the blood. Such a mechanism results in the patency beginning to decrease as soon as the coating contacts the clotting agents of the blood, and it is only a matter of time before filter patency is reduced or eliminated by the clotting agents.

Two other mechanisms in the prior art used to provide for increased filter patency include dipping the filter in an anti-coagulant such as heparin solution, or a systemic use of drugs such as a IIb/IIIa inhibitor. Even with dipping in heparin, the patency of the filter will deteriorate over a relatively short period of time. Problems with systemic use of drugs may manifest themselves as excessive patient bleeding.

SUMMARY OF THE INVENTION

The present invention is a protection device with a local drug delivery system. The drug delivery system delivers a drug for increasing filter patency. The protection device includes a hostwire to which an expandable filter is mounted, and an embodiment of an improved drug delivery mechanism for facilitating filter patency is described herein.

Local drug infusion helps to maintain patency of the filter while blood is flowing through the filter. Local drug infusion provides the effects of the drug in a local concentration where needed, to maintain filter patency while minimizing the possible side effects (i.e. excessive bleeding) that the drug could cause if used systemically. Generally, the drug is delivered upstream of the filter, proximate the filter, and allowed to flow distally, through the filter with the blood.

A first embodiment of the present invention is a drug delivery mechanism comprising a micro-electro mechanical system (MEMS) on or in a guide coil. The guide coil is wound about the hostwire either proximal or distal to the filter or both. The MEMS is positioned near a first end of the guide coil. The MEMS is able to automatically advance toward the second end of the guide coil by ratcheting a predetermined distance along the guide coil. The guide coil may be a shape memory tubular body containing a drug. As the MEMS ratchets along a length of the coil, the drug is released from the guide coil. The drug is then delivered to the filter so as to induce continued filter patency.

Another embodiment of the present invention utilizes a MEMS on a guide wherein packets or beads containing a drug are on the surface of the guide. As the MEMS ratchets along the surface of the guide, the packets or beads are pierced, thus causing the release of the drug.

Still another embodiment of the present invention utilizes a drug delivery system comprising drug eluting beads. The beads may be located on the hostwire, within the filter, electrospun to the filter, distal to the filter and/or proximal to the filter or a combination thereof. The beads are solid forms of variable shape that allow a drug to be harbored on or within the bead such as in a crevice, pore, surface, underneath or within a coating, dissolved into the bulk of the bead, or any other such means of harboring a drug. The beads may release the drug on deployment of the protection device or under predetermined environmental or biological conditions that induce the release of the drug. The drug may be released such as by piercing of the beads, dissolving of a coating on the beads, or any other suitable method of activating the delivery of a drug. The beads may be activated by piercing where the beads are released from the hostwire and allowed to impact the filter causing the beads to be pierced. The drug would then be released on the filter so as to automatically induce increased filter patency without physician or operator intervention. The beads may also have a coating or a shape or form that regulates or controls the release of the drug and deliver the drug to the filter such as by a stimuli sensitive polymers or other such coatings.

Another embodiment of the present invention comprises a hydrogel or a gel conjugate that is used to coat the filter and/or hostwire. The gel acts as a drug delivery system wherein the gel may be activated by environmental or biological agents or variables such as ph, temperature, pressure differential, precursors to fibrin formation, and the like.

Another embodiment of the present invention has a drug delivery mechanism received within a lumen of a tubular member for providing local drug infusion such as through a plurality of weep holes at a distal portion of the tubular member. An expandable bladder is located within the hollow portion. The bladder expands upon the occurrence of a predetermined environmental condition such as temperature or pressure differential or inflation with a syringe. The drug occupies the lumen with the tubular member. As the bladder expands the drug is released through weep holes through a wall defining the tubular member and delivered to the filter.

The present invention thereby provides for a local drug delivery mechanism for providing a drug to a protection device such as a filter for inducing and facilitating filter patency frequently without requiring interaction from a physician or operator.

DETAILED DESCRIPTION OF PREFERRED EMBODIMENTS

Figure 1:
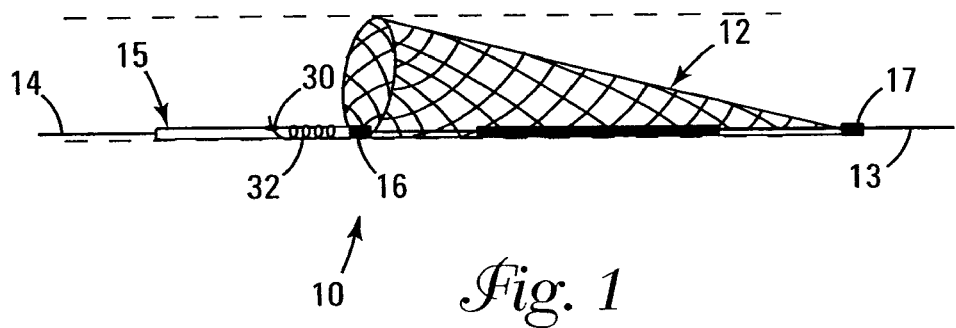
FIG. 1 is a side view of a protection device with a microelectro mechanical system for providing drug delivery.

FIG. 1 illustrates a first embodiment of a protection device 10 with a drug delivery mechanism 15 for automatically delivering a drug without operator or physician input. The protection device 10 is shown having a filter 12 that can be expanded or collapsed about a hostwire 14. The drug delivery mechanism 15 includes a coiled tube 32 helically wound with respect to an axis of elongation defined by the hostwire 14. Also shown, is a proximal marker band 16 and a distal marker band 17.

FIG. 1 depicts only the distal portion 13 of the hostwire 14, wherein the term 'distal' refers to the downstream end of the hostwire 14 with respect to flow in the body vessel, and the term 'proximal' refers to the upstream end with respect to flow in the vessel.

Use of the protection device 10 includes advancing the protection device 10 within a lumen and expanding the protection device to engage a wall of the lumen. Once expanded, the filter 12 is able to filter fluid flowing through the lumen so as to prevent particulate matter from passing distal to the filter 12. Most commonly, the protection device 10 is used to filter particulate matter entrained in blood such as in a blood vessel of a patient's vascular system.

The drug delivery mechanism 15 is configured to deliver the drug to the device 10 such as by leaching or metered methods that occur automatically without physician input once the protection device 10 and/or filter 12 is deployed. When used in the vascular system, the filter 12 may become at least partially occluded as a result of blood coagulation and/or clotting. Upon delivery of the drug to the protection device 10 by the drug delivery mechanism 15, the drug is able to induce or facilitate continued filter patency.

The drug delivery system embodied in FIG. 1 is a microelectro mechanical device (MEMS) 30. The MEMS 30 is positioned proximal the filter 12. The MEMS 30 is positioned on a guide 32 such as a coiled tube 32. The guide 32 is positioned about an axis of elongation defined by the hostwire 14. The MEMS 30 is able to ratchet along the length of the guide 32. The drug is dispensed and delivered by the MEMS 30 as the MEMS 30 advances at predetermined intervals along the length of the guide 32. It is contemplated that the MEMS 30 begin at or near a first end of a corresponding guide 32 and ratchet in the direction of a second end of the corresponding guide 32. Alternatively, the guide could be straight wire or tube running parallel to the hostwire, or could be the hostwire itself.

Figure 2:
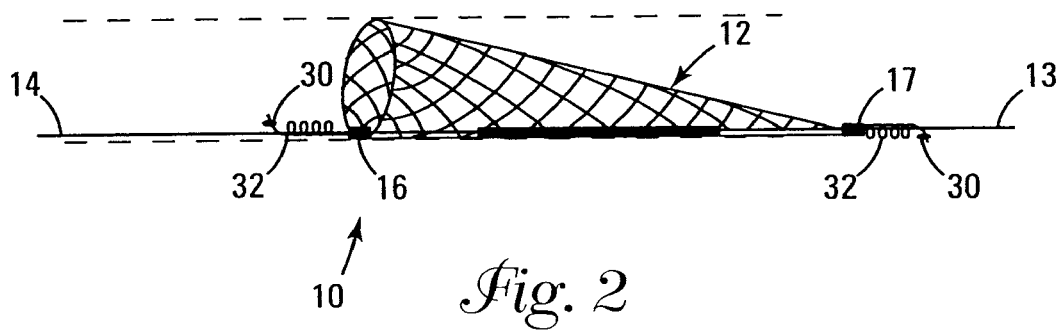
FIG. 2 is a side view of a protection device with a plurality of electro mechanical systems for providing drug delivery.

FIG. 2 illustrates a plurality of MEMS 30 utilized as a drug delivery mechanism 15. A first MEMS 30 may be positioned proximal to the filter 12 and a second MEMS 30 may be positioned distal to the filter 12. As illustrated, each MEMS 30 is positioned on a guide 32 such as a coiled tube 32. Each MEMS 30 is able to ratchet along the length of the guide 32. The drug is dispensed and delivered by each MEMS 30 at predetermined intervals.

It is further contemplated that the drug delivery mechanism 15 may, instead, comprise only a single MEMS 30 and guide 32 such that the guide 32 and MEMS 30 are positioned distal to the filter 12.

Figure 3:
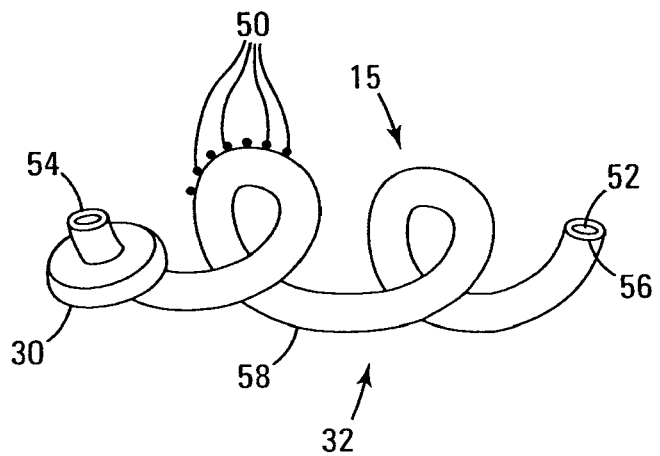
FIG. 3 is a magnified side view of an electro mechanical system and guide member.

FIG. 3 illustrates a magnified view of a MEMS and coil drug delivery system 15. The function of the drug delivery system 15 is to deliver a drug to the filter to facilitate patency of the filter 12. The drug is released by the movement of the MEMS 30 along the length of the guide 32. For example, the drug may be located within a lumen 52 or other such compartment within the guide 32. As the MEMS 30 ratchets along the length of the guide 32 from a first end 54 toward a second end 56, the drug is forced or induced out the second end 56 of the guide 32 and released into the blood stream or onto the protection device 10 and/or filter 12. It is beneficial, but not necessary, that the second end 56 of the guide 32 be the end nearest the filter 12 for greatest benefit toward facilitating filter patency.

The guide 32 may be a coil made of a shape memory material such as an alloy or from a drug-loaded shape-memory polymer material. The MEMS 30 may be positioned over the guide 32 or marker band 16 or hostwire 14, and may have a shape such as a donut shape that slides along the delivery guide 32.

Alternatively, the coiled tube 32 could be made of a shape memory polymer and drug loaded such that the drug is released upon a reaction to pressure, temperature, flow characteristics such that the drug may be released from a storage portion 52 within the tube without the use of the MEMS.

Another method for drug delivery using the MEMS 30 and guide 32 utilizes drug packets and/or beads 50. For example, packets of the drug may be located on the surface 58 of the guide 32. As the MEMS 30 advances from the first end 54 toward the second end 56 of the guide 32, over the packets 50, the packets 50 are pierced or broken causing the packets to dispense or release the drug. For this drug delivery system 15 it is beneficial, but not necessary, that the first end 54 of the guide 32 be nearest the filter 12 with respect to the second end 56. The reason being that the drug is released after the MEMS 30 ratchets over the packet 50.

The drug delivery system comprising the MEMS 30 and guide 32 may be positioned proximate or adjacent to the filter 12. The drug may be released or delivered directly onto the filter 12, marker band 16, and/or hostwire 14. Alternatively, the drug may be released or delivered into the bloodstream of a patient and allowed or directed to flow to the filter 12.

The initiation of the drug delivery system may occur upon deployment of the protection device 10. Prior to deployment of the protection device 10, the filter 12 is collapsed toward the hostwire 14. In this collapsed configuration, the coil 32 may be deformed or maintained in a predetermined position on the guide 32 so as to prevent the MEMS 30 from advancing. Once the filter 12 is expanded, the coil 32 can resume its preformed state that allows the MEMS 30 to become self-activated and begin dispensing the drugs for inducing continued patency of the filter 12. Self-activation of the drug delivery mechanism may occur by any such method wherein deployment of the filter 12 functions to remove any restriction on the MEMS 30 from advancing along the guide 32.

The drug released by the drug delivery mechanism 15 may be any such drug that prevents clotting of the blood or otherwise induces or facilitates continued filter patency, such as heparin, Integrilin, Aggrastat, or fibrinolytic drugs Such drugs may react with blood platelets, blood clotting agents, precursors to the formation of blood clots, and any other agents having a role in the formation of blood clots, coagulation, and reversal of same.

The drug may be dispensed at predetermined intervals by the MEMS 30 where the MEMS 30 ratchets a predetermined length along the guide 32 at predetermined time intervals resulting in the dispensing of the drug at periodic intervals.

A hydrogel, or other leachable coating laden with a drug can be delivered and/or applied to the filter 12, marker bands 16, and/or the hostwire 14 proximal to the filter 12. This can also be applied to the inside or outside diameter of a guide catheter used to deliver the protection device 10 to a location within a patient's vascular system, for example. Some drug methods common to those of ordinary skill in the art include pe-dipping with albumin, heparin or calcium channel blockers. Hydrogels in combination with drugs can be used alone or in combination with MEMS. The methods for making a MEMS 30 as described herein are common to those of ordinary skill in the art as is the use of various drugs that may be delivered by the MEMS 30 to facilitate patency of the filter 12 and protection device 10.

The MEMS 30 may have any shape, such as a short-tubular or donut shape in the preferred embodiment. Any shape may be used that allows the MEMS 30 to advance along the guide 32 and release drugs for continued patency of the filter 12. The guide 32 may likewise have any shape that allows the MEMS 30 to ratchet along the guide 32 so as to provide a drug delivery mechanism 15 to the protection device 10.

Figure 4:
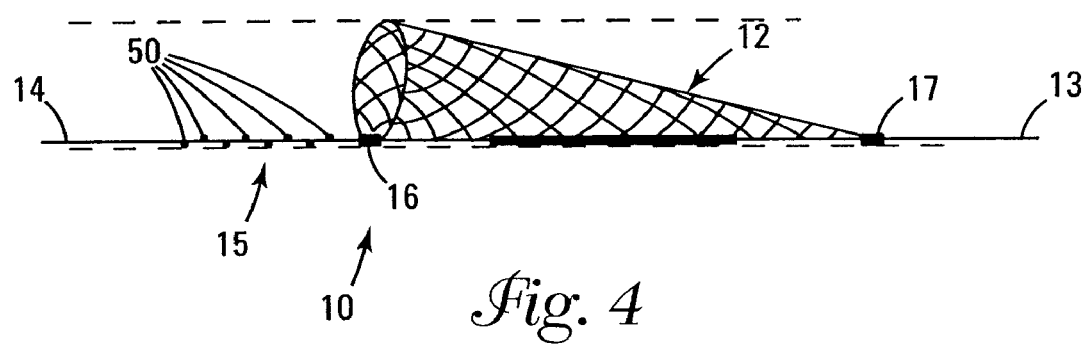
FIG. 4 is a side view of a protection device with drug eluting beads on the hostwire.
Figure 5:
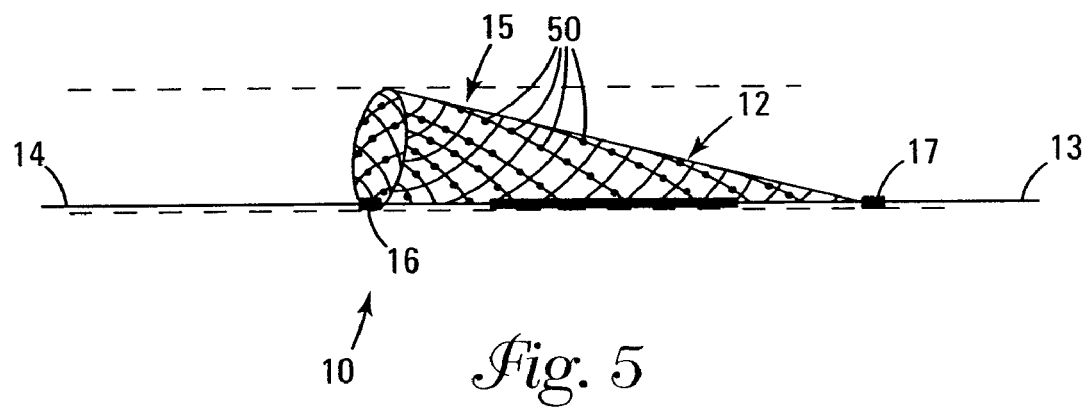
FIG. 5 is a side view of a protection device with drug eluting beads spun about the expandable filter.
Figure 6:
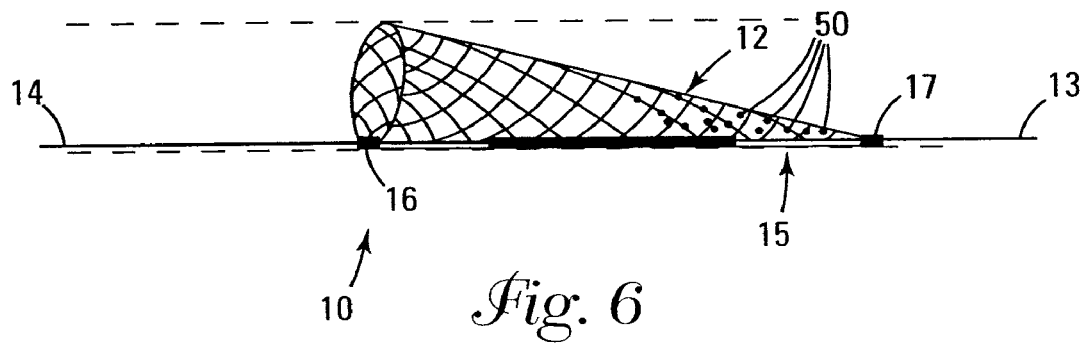
FIG. 6 is a side view of a protection device with drug eluting beads positioned within the expandable filter.

FIGS. 4-6 illustrate yet another embodiment of the present invention. As in FIGS. 1-3, a protection device 10 is shown having an expandable filter 12 attached proximate the distal end of a hostwire 14. The filter 12 has proximal and distal marker bands 16, 17 on respective sides. The drug delivery mechanism 15 in this embodiment is a polymer containing structure illustrated in the figures as drug eluting beads 50. It will be understood, however, that structures shaped other than as "beads" would be acceptable. The beads 50 which are shown may be positioned on the hostwire 14 as shown in FIG. 4. Fibers attached to the filter 12 as in FIG. 5, can have the drug mixed with a polymer. FIG. 6 illustrates a multiplicity of beads received within a capture space of filter 12. These examples are illustrative, however, and not limiting as to the use of drug eluting structures for delivery of a drug to induce continued patency within a filter 12. Each embodiment illustrated is discussed separately below.

FIG. 4 shows an alternative drug delivery apparatus comprising a hostwire 14 extending through a filter 12, and drug eluting beads 50 mounted on the hostwire 14. The drug eluting beads 50 may be pierced during deployment resulting in release of the drug. Alternatively, the drug could be permitted to leach out of the beads or other polymer containing structure. Piercing of the drug eluting beads 50, when piercing is utilized, may occur upon deployment of the filter 12 to the expanded configuration. For example, the drug eluting beads 50 may be affixed to the hostwire 14 such that when the filter 12 is deployed, the beads 50 will be pierced by the wires of the filter 12. The beads 50 may alternatively be pierced where, upon deployment, the beads 50 are released from the hostwire 14 and allowed to flow, project, or travel into the filter 12. As the beads 50 impact strands forming the filter 12, the beads 50 may become pierced by the filter strands, thus causing the release of the drug for continued filter 12 patency.

FIG. 5 illustrates the drug eluting beads 50 attached to strands of the filter 12. The beads 50 may be formed by spinning polymer strands onto the filter 12 and then post processing the strands to form beads. Such beads can be formed on the filter or into the filter. Such beads 50 may be a polymer material intermixed or absorbed or filled with the drug such that instead of creating a polymer strand during the forming process, they create a polymer bead containing the drug for facilitating patency of the filter 12. Alternatively, the fibers can have the drug mixed immediately with the polymer.

FIG. 6 illustrates drug eluting beads 50 positioned within a capture space of the filter 12. The drug eluting beads 50 would have a diameter greater than the filter pores so that the beads 50 are maintained within the filter 12.

The beads 50 are self-activating such that the drug may be delivered during deployment of the protection device 10 or filter 12. The initiation of the drug release may be activated either by piercing of the beads 50 or by interaction of the beads 50 and/or drug with the environment in which the protection device 10 is deployed, such as agents in blood that may initiate activation of the drug or the release of the drug, such as by the drug leaching out of the beads 50.

The drug eluting beads 50 may be composed of a polymer material. The drug may be contained within the beads 50 or coated about the surface of the beads 50 or within pores within the beads, dissolved in the beads, or a combination thereof. The drug eluting beads 50 may have a coating thereon, such that the drug is eluted only after the coating is pierced or activated by leaching out of the beads 50. Thus, a self-activating coating may be used to prevent release of the drug until intended activation of the drug delivery mechanism such as by an activating agent found in blood. The coating may further be dissolved by an activating agent in the blood such as platelets or other precursors to coagulation. The drug delivery method using beads 50 may include immediate drug delivery once the device is deployed, or timed release of the drug continuing over a 30 to 60 minute, or longer, time period, or a variable release time depending on the material and configuration.

The beads 50 may be porous or non-porous, and take on many shapes such as that of a rod, sphere, oval, and the like. Further, the beads 50 may be located on the coil or guide 32 such as for use with an MEMS 30, as in FIG. 1. The drug may be a smart-release or passive release. The above examples of drug eluting beads 50 are illustrative and not limiting as to the use of beads 50 as the drug delivery mechanism to induce continued patency of the filter 12.

Figure 7:
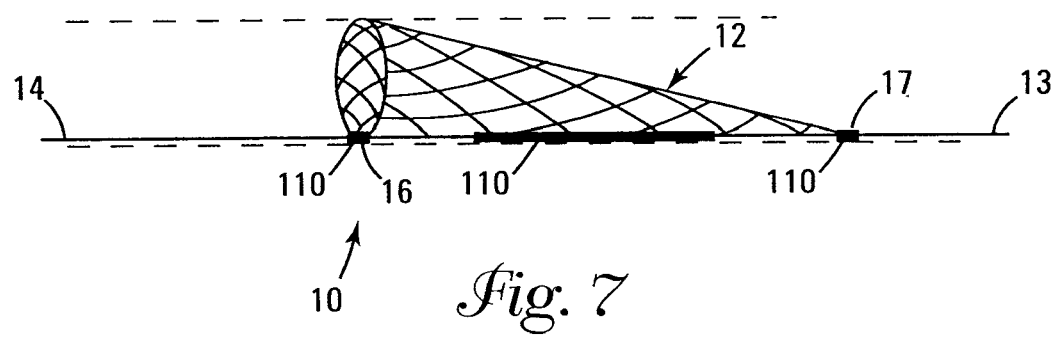
FIG. 7 is a side view of a protection device having a drug coating.

FIG. 7 illustrates yet another embodiment of the present invention. A drug coating 110 is placed on protection device 10 proximate the filter 12, illustrated by the areas identified by reference numeral 110 in FIG. 7. The coating 110 may be positioned on the hostwire 14, marker bands 16, the filter itself, in combination or alternatively on surface of the protection device 10. The coating 110 may be a hydrogel or other such coating. The hydrogel coating may act similar to the beads 50, previously discussed, wherein the hydrogel contains a drug or is coated with a drug such that the hydrogel acts as a drug delivery mechanism. The drug may also be smart released or passively released depending on the characteristics of the drug, hydrogel, coating, or combination thereof.

Drugs can also be incorporated into a gel conjugate located proximal to the filter 12 such as in conjunction with the other embodiments of the present invention. The gel conjugate viscosity could be selected to decrease with body temperature, so as to induce the release of the drug once placed in the body. Alternatively, a saturated sponge or patch placed just proximal to the filter could release the drug.

While the drug could be released passively by infusion, dissolution or leaching, as described above, the need for providing a drug at certain intervals could also be addressed. This could be accomplished by the use of barrier technologies, (i.e. a film over the drug) to control the kinetics of the drug release. The thickness of the film could vary in regions of the device so the drug would be released in different amounts and/or at different places at various time intervals.

Drug release may also be controlled by a change in environmental conditions such as a pressure drop across the device, causing increased drug release as the device becomes occluded. Stimuli sensitive polymers (SSP's) are currently available as coatings that are capable of responding to their environment and controlling the delivery of functional substances. The SSP fibers may be swollen with water so as to entrap an active substance. When there is an environmental change such as temperature, pH, light, salt, electrical field or stress, the collapse of the SSP acts as a self-activating mechanism for releasing the drug. The environmental change may be a change in viscosity or pressure caused by platelet activation and aggregation followed by coagulation leading to fibrin formation in the blood of the patient's vascular system. The SSP fibers could incorporate the drug eluting beads 50 discussed above such as by entrapping the beads 50 in the SSP fibers. The beads 50 may then be released when there is a change in condition of the bloodstream viscosity or pressure indicating the onset of filter 12 occlusion. Such a change in conditions would activate the drug delivery mechanism and release the beads 50 and drugs therein.

The formation of thrombus often occurs distal to the filter 12, in the areas of stagnant and/or disrupted blood flow patterns. Thus, the drug delivery methods discussed herein may be positioned distal to the filter 12 to address this problem. Additionally, flow re-directors could be placed distal to the filter 12 so as to encourage the drug to remain concentrated around the filter 12. An example of such a flow re-director is a variable size vascular plug placed distal to the filter 12 to be used as a regulator of flow and/or pressure across the filter 12. Such control of flow in combination with a drug delivery system may further facilitate filter 12 patency.

Figure 8:
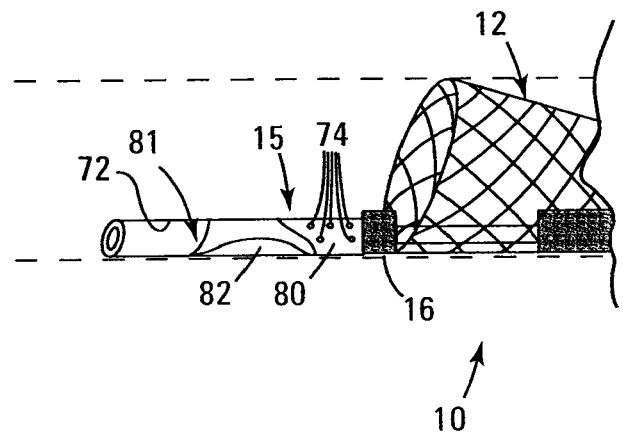
FIG. 8 is side view of a protection device with a hollowed portion with an expandable bladder for drug delivery.

FIG. 8 illustrates another embodiment of a drug delivery device for delivering a drug to a protection device 10 for maintaining filter 12 patency. In this embodiment, an expandable bladder 82 is used to infuse the drug from a reservoir or cavity 80, defined by a lumen 72 through hostwire 14, through a plurality of delivery ports 74. The bladder 82 is expanded within lumen 72 to force the drug positioned within the reservoir 80 to pass through a delivery portion where the drug is released through weep holes or ports 74. Once the drug is delivered through the ports 74 it is able to be locally delivered to the filter 12 of the protection device 10 and the area surrounding the filter 12.

As illustrated, the delivery ports 74 may be a plurality of apertures 74 spaced about the side wall 76 of the reservoir 80. The apertures 74 form channels from the interior of the lumen 72 to the exterior of the side wall 76 for allowing the drug to be delivered from within the lumen 72 to the exterior of the tubular member 81. The drug delivery mechanism 15 may deliver the drug by expanding within the lumen 72 (for example, as a result of increased temperature) thereby forcing the drug to exit the reservoir 80 and the delivery ports 74. As the drug is released from the lumen 72 it is able to be delivered to the filter 12 portion of the protection device 10. The drug is then able to facilitate continued patency of the filter 12.

As illustrated in FIG. 8, the drug delivery mechanism 15 may be activated by the infusion of the drug delivery portion 80 with the drug from the expansion of an expandable bladder 82. The bladder 82 may be an inflatable member such as a balloon that is pre-inflated and affixed to the interior of the tubular member The exit ports 74 allow for the drug to be channeled therethrough to the outer surface of the wall of the drug delivery structure. As the bladder 82 expands due to flow of drug through the apertures, the pressure within the bladder and within the hollow portion 80 decreases. The rate of expansion of the bladder 82 may be controlled so as to control the rate at which the drug is delivered from the device. For example, a bladder pre-inflated at low pressure will result in a slower release of the drug than a bladder pre-inflated at high pressure.

The tubular member 81 is a generally cylindrical tube having a side wall 76 with an inner lumen 72 extending therewithin. The tube 81 has a plurality of apertures 74 formed through at the side wall 76 of the tubular member 81 allowing communication of a substance within the inner lumen 72 to the exterior of the side wall 76 The apertures 74 are spaced about the circumference of the side wall 76 and may have various diameters and be of a size and number to control the release rate of the drug in cooperation with bladder pressure. The side wall 76 has an elongate dimension wherein the plurality of apertures 74 may be spaced along at least a portion of the elongate dimension. The apertures 74 may be staggered along the side wall circumference, such as in a spiral pattern, a ring pattern, or any other such combination random or ordered, over the side wall 76. A portion of the side wall 76 may be tapered outwardly.

Methods of delivering the drug include a pump powered by induction, a screw-drive, an elastomer drive, or blood flow. The electromotive force or peristaltic action provided by the heart may also be used to drive the drug delivery mechanism 15. Alternatively, osmotic, hypertonic or capillary action could function as the driving force to pump the drug through the tubular member. Any mechanism capable of providing a driving force to the drug may be employed such as the use of temperature or ultrasound to initiate such driving force.

The tubular member 81 may allow the drug to be dispensed into the lumen 72 and/or maintained within the drug delivery portion of the device and delivered through the weep holes 74 in the wall 76 of the tubular member 81. The weep holes 74 are spaced within the wall 76 of the tubular member 81. A plurality of tubes may be incorporated having a corresponding plurality of sidewalls and each tubing having a predetermined number of apertures.

Figure 9:
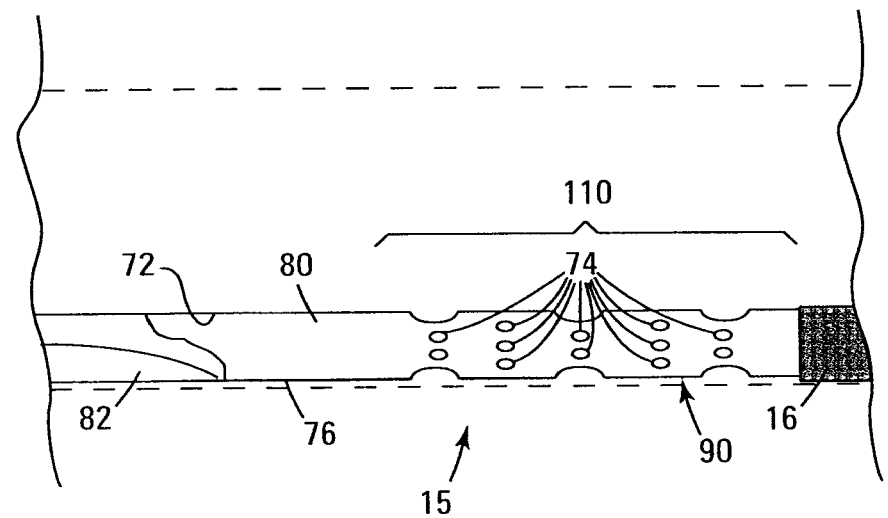
FIG. 9 is a side view of a protection device with a fluted hollow portion.

FIG. 9 illustrates a reservoir 80 that has a fluted portion 90 to increase surface area on which coating capacity can be maximized. It is contemplated that such a fluted lumen could be employed in the embodiment illustrated in FIG. 7. The fluted portion 90 can be coated along a length as at reference numeral 110 or a longer or shorter length, as appropriate.

Figure 10:
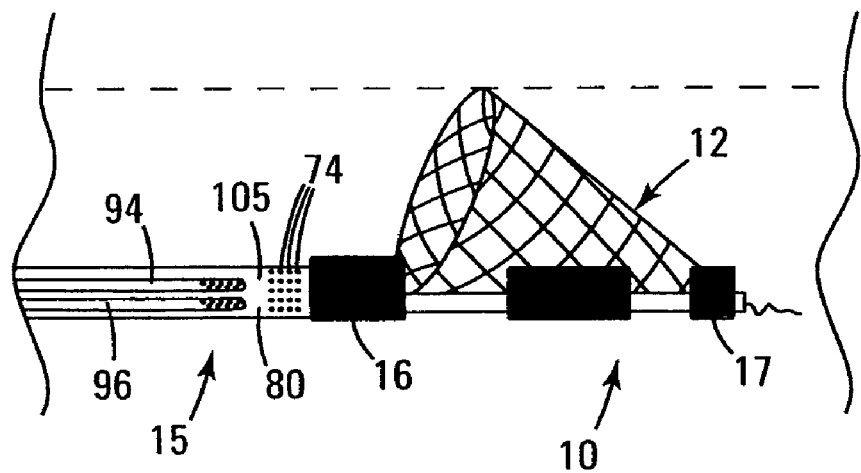
FIG. 10 is a side view of a protection device having adjacent lumens for drug delivery.
Figure 11:
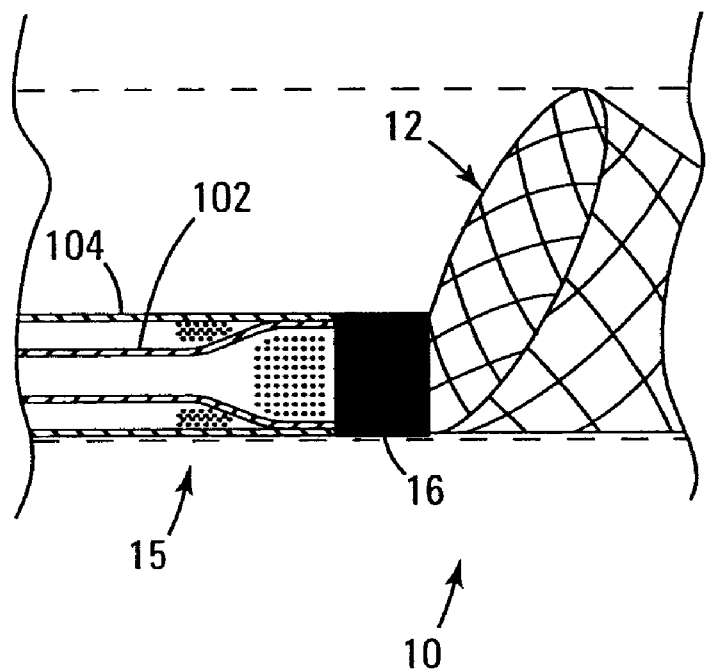
FIG. 11 is a side view of a protection device having coaxial lumens for drug delivery.

Turning now to FIGS. 10-11, it is contemplated that the drug delivery mechanism illustrated in FIG. 8 may have more than a single lumen 72. For example, FIG. 10 illustrates a first lumen 94 adjacent a second lumen 96. Each lumen 94, 96 may be capable of delivering a drug therefrom. It is contemplated that each lumen may be capable of delivering a different drug or that each lumen be capable of delivering a component of a drug capable of mixing with the component in the adjacent lumen. It is further contemplated that any number of adjacent lumens may be incorporated into the drug delivery portion 80.

FIG. 11 illustrates a drug delivery mechanism 15 having a coaxial lumen 100 such that a first lumen 99 extends coaxially relative to a wall 104 second coaxial lumen 100. Thus, each drug delivery lumen may have at least a single wall 76 with a plurality of weep holes 74, wherein the drug delivery mechanism may have a plurality of side walls 76. The use of more than one lumen for simultaneous infusion of more than one drug for in situ mixing can be employed to inhibit reactions during the intrinsic or common pathway of fibrin clot formation or platelet activation and/or aggregation. The multiple lumens may be individually, sequentially or simultaneously infused. The tubular member, guide catheter (not shown) or an accessory catheter(not shown) could be charged with a reservoir of drugs.

The delivery ports 74 may be spaced in a variety of arrangements on the side wall 76 of the respective tubular members as illustrated in FIGS. 10-11.

Alternatively, if a plurality of side walls are present, the delivery ports 74 may be spaced in alternative configurations on each side wall 76. For example, the delivery ports 74 may be spaced circumferentially at various along the length of the wall, the ports 74 may be arbitrarily patterned along the length of the wall, the ports 74 may be spaced so as to helically wind about the length of the wall, and any combination or other such means of spacing, random or ordered so as to provide a plurality of delivery ports 74 about the side wall of the lumen 72 for delivering of a drug from the lumen 72.

The spacing and sizing of the apertures 74 may be configured to control the rate of diffusion of the drug into the blood vessel. The apertures 74 may have a predetermined size and spacing that allows for a slower or faster relative rate of diffusion. Controlling the rate of diffusion may lessen the shear stresses on blood flowing toward the filter 12. A lesser shear stress is preferable over a high pressure drug delivery that may create an accelerated flow pattern that could be detrimental to flow dynamics surrounding the filter 12.

After the drug is delivered through the delivery port 74 it is able to become infused within the fluid flowing on the outer surface of the tubular member 81. For example, if the tubular member 81 is positioned within a blood stream the drug will become infused within the blood stream. As the blood stream is flowing toward the filter 12, the filter 12 being downstream, the drug will likewise be delivered to the filter 12 from a upstream location thus providing for local drug delivery. Alternatively, the lumen 94 may be located adjacent to another lumen 96. The drug would then be delivered into the lumen 105 and be able to flow and intermix with the fluid, such as a drug or component, within the lumen 105. The combination of the drugs from the first and second lumens 94, 96 may then be delivered into a fluid external to the lumen 105, such as the blood within a blood vessel.

In another alternative, the first tubular member 102 may be coaxial with a second tubular member 104. Thus the drugs within the first and second tubes 102, 104 may be delivered into the bloodstream directly without intermixing prior to passage through ports 74, so as to mix and be delivered externally to the filter 12. As the drug is delivered into a fluid such as blood, it is able to be delivered with the flow of fluid to distal portions of the protection device 10, preferably to the filter 12. The drug may provide for an increased concentration of anti-coagulants, or other such drugs preventing formation of thrombi and occlusions of the filter 12. The local concentration of the drug may also cover portions of the drug delivery mechanism 15 and tubular members and portions of the protection device 10 that are proximal and distal to the filter 12. Infusing the drug upstream from the filter 12 and allowing it to flow to the filter 12 may also deliver the drug to local stasis areas in the vicinity of the filter 12 where it can minimize and/or prevent clotting and/or coagulation. This may flush loose partially adherent emboli, that may otherwise become dislodged during or after filter 12 removal, into the filter 12 along with the drug delivery medium.

The shape, size, and workings of the filter 12 are not critical to the efficacy of the present invention. The filter 12 used in the embodiments of the present invention is contemplated as a possible type of filter 12 to be used with the present invention. However, the filter 12 may assume a variety of configurations such as a basket, a windsock, a flat shape, and elongated shape, the filter 12 may have a cover or an alternating periphery or diameter. The filter 12 must merely perform the function of preventing the passage of particulate material of a predetermined size. The present invention addresses the delivery of a drug to a filter 12 to facilitate filter patency, and contemplates the drug delivery system disclosed herein as incorporating a variety of filter sizes, shapes and configurations. The filter 12 may be attached to the distal portion of a hostwire 14. The hostwire 14 may extend through the lumen 72 containing the drug. Alternatively, the hostwire 14 may have a hollow portion 80 for containing and delivering the drug therefrom.

Possible drugs to be used in the present invention include IIb/IIIa inhibitors and any other such anti-platelet agents, or drugs for preventing occlusions to the filter 12 during a medical procedure, such as heparin, Aggrastat or Integrilin or fibrinolytic drugs. The drugs may be precursors or drug agents to be mixed with other fluids so as to effect the purpose of the present invention. For example, a drug in a first lumen 72 may not be capable of preventing occlusion unless or until mixed with a drug in the second lumen 72 or when mixed with blood, for example. Such drugs help to maintain filter 12 patency even with reduced filter 12 pore sizes without negative effects of systemic drug administration such as excessive bleeding.

In summary, an advantage of the present invention is increased patency, such as the length of time patency is maintained within the filter, or the degree of patency allowed as a result of drug delivery to the protection device. This gives the operator or physician additional time to perform a medical procedure, thus making the procedure safer for the patient.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A vascular protection device for use in the vasculature of a patient comprising:
   a hostwire having a distal portion, the hostwire interposable in the vasculature of the patient;
   an expandable filter attached to a distal portion of the hostwire, the filter being expandable from a collapsed delivery configuration to an expanded deployed configuration, the filter having a proximal end, a distal end and a filtering surface for allowing passage of blood therethrough, the filtering surface not carrying a drug in the collapsed delivery configuration; and
   a drug delivery mechanism carried by the hostwire adjacent the distal portion of the hostwire, the drug delivery mechanism being positioned proximal to the distal end of the filter and being spaced apart from the filtering surface of the filter when the filter is in the expanded deployed configuration in the patient's vasculature, the drug delivery mechanism including a drug, the drug delivery mechanism being configured to release an amount of the drug into blood flowing in the vasculature sufficient to facilitate maintaining patency of the filter during use of the filter in the patient's vasculature, the drug comprising an agent formulated to prevent blood clotting.

2. The vascular device of claim 1, wherein the drug delivery mechanism is positioned proximal to the proximal end of the filter.

3. The vascular device of claim 1, wherein the drug delivery mechanism is self-activating.

4. The vascular device of claim 3, wherein the self-activating drug delivery mechanism includes a plurality of beads.

5. The vascular device of claim 4, wherein the self-activating drug delivery mechanism is activated by piercing of the beads upon deployment of the vascular device.

6. The vascular device of claim 4, wherein the self-activating drug delivery mechanism is activated by dissolving a coating applied to the beads.

7. The vascular device of claim 4, wherein the filter is expandable about the hostwire.

8. The vascular device of claim 7, wherein the plurality of beads are carried by the hostwire.

9. The vascular device of claim 8, wherein the self-activating drug delivery mechanism is activated by releasing the beads from the hostwire and impacting the beads against the filtering surface of the filter.

10. The vascular device of claim 3, wherein the self-activating drug delivery mechanism is a micro-electro mechanical system (MEMS).

11. The vascular device of claim 10, wherein the MEMS dispenses the drug at predetermined intervals.

12. The medical device of claim 11, wherein said MEMS is located on a hostwire extending proximate said distal member of said medical device.

13. The vascular device of claim 3, wherein the self-activating drug delivery mechanism includes an expandable bladder and wherein the self-activating delivery mechanism is activated by expansion of the expandable bladder.

14. The vascular device of claim 6, wherein the coating is dissolved by an activating agent in the blood of a patient.

15. The vascular device of claim 4, wherein at least a portion of the beads are porous.

16. The vascular device of claim 4, wherein at least a portion of the plurality of beads comprise a polymer.

17. The vascular device of claim 1, wherein the drug is an anti-platelet agent.

18. The vascular device of claim 1, wherein the drug is a IIb/IIIa inhibitor.

19. The vascular device of claim 1, wherein the drug is a fibrinolytic drug.

20. The vascular device of claim 1, wherein the drug is selected from heparin, Aggrastat and Integrilin.

21. A vascular protection device for use in the vasculature of a patient comprising:
   a hostwire having a distal portion, the hostwire interposable in the vasculature of the patient;
   an expandable filter attached to a distal portion of the hostwire, the filter being expandable from a collapsed delivery configuration to an expanded deployed configuration, the filter having a proximal end, a distal end and a filtering surface for allowing passage of blood therethrough; and
   a drug delivery mechanism carried by the hostwire adjacent the distal portion of the hostwire, the drug delivery mechanism being positioned proximal to the distal end of the filter and being spaced apart from the filtering surface of the filter when the filter is in the expanded deployed configuration in the patient's vasculature, the drug delivery mechanism including a drug, the drug delivery mechanism being configured to release an amount of the drug into blood flowing in the vasculature sufficient to facilitate maintaining patency of the filter during use of the filter in the patient's vasculature, the drug comprising an agent formulated to prevent blood clotting,
   wherein the drug delivery mechanism is self-activating,
   wherein the self-activating drug delivery mechanism includes a plurality of beads, and
   wherein the self-activating drug delivery mechanism is activated by piercing of the beads upon deployment of the vascular device.

22. The vascular device of claim 21, wherein the drug delivery mechanism is positioned proximal to the proximal end of the filter.

23. The vascular device of claim 21, wherein the filter is expandable about the hostwire.

24. The vascular device of claim 23, wherein the plurality of beads are carried by the hostwire.

25. The vascular device of claim 21, wherein at least a portion of the beads are porous.

26. The vascular device of claim 21, wherein at least a portion of the plurality of beads comprise a polymer.

27. The vascular device of claim 21, wherein the drug is an anti-platelet agent.

28. The vascular device of claim 21, wherein the drug is a IIb/IIIa inhibitor.

29. The vascular device of claim 21, wherein the drug is a fibrinolytic drug.

30. The vascular device of claim 21, wherein the drug is selected from heparin, Aggrastat and Integrilin.

31. A vascular protection device for use in the vasculature of a patient comprising:
   a hostwire having a distal portion, the hostwire interposable in the vasculature of the patient;

an expandable filter attached to a distal portion of the hostwire, the filter being expandable from a collapsed delivery configuration to an expanded deployed configuration, the filter having a proximal end, a distal end and a filtering surface for allowing passage of blood therethrough; and a drug delivery mechanism carried by the hostwire adjacent the distal portion of the hostwire, the drug delivery mechanism being positioned proximal to the distal end of the filter and being spaced apart from the filtering surface of the filter when the filter is in the expanded deployed configuration in the patient's vasculature, the drug delivery mechanism including a drug, the drug delivery mechanism being configured to release an amount of the drug into blood flowing in the vasculature sufficient to facilitate maintaining patency of the filter during use of the filter in the patient's vasculature, the drug comprising an agent formulated to prevent blood clotting, wherein the drug delivery mechanism is self-activating, wherein the self-activating drug delivery mechanism includes a plurality of beads, wherein the filter is expandable about the hostwire, wherein the plurality of beads are carried by the hostwire, and wherein the self-activating drug delivery mechanism is activated by releasing the beads from the hostwire and impacting the beads against the filtering surface of the filter.

32. The vascular device of claim 31, wherein the drug delivery mechanism is positioned proximal to the proximal end of the filter.

33. The vascular device of claim 31, wherein at least a portion of the beads are porous.

34. The vascular device of claim 31, wherein at least a portion of the plurality of beads comprise a polymer.

35. The vascular device of claim 31, wherein the drug is an anti-platelet agent.

36. The vascular device of claim 31, wherein the drug is a IIb/IIIa inhibitor.

37. The vascular device of claim 31, wherein the drug is a fibrinolytic drug.

38. The vascular device of claim 31, wherein the drug is selected from heparin, Aggrastat and Integrilin.

* * * * *